United States Patent
Si et al.

(10) Patent No.: US 9,682,907 B1
(45) Date of Patent: Jun. 20, 2017

(54) GREEN PREPARATION METHOD FOR TRIFLUOROCHLOROETHYLENE

(71) Applicant: CHANGSHU 3F FLUORINE CHEMICAL CO., LTD., Jiangsu (CN)

(72) Inventors: Linxu Si, Jiangsu (CN); Pingzhong Zhang, Jiangsu (CN); Hexiang Gu, Jiangsu (CN)

(73) Assignee: Changshu 3F Fluorine Chemical Co., LTD., Jiangsu (CN)

( * ) Notice: Subject to any disclaimer, the term of this patent is extended or adjusted under 35 U.S.C. 154(b) by 0 days.

(21) Appl. No.: 15/325,895

(22) PCT Filed: Dec. 9, 2014

(86) PCT No.: PCT/CN2014/093346
§ 371 (c)(1),
(2) Date: Jan. 12, 2017

(87) PCT Pub. No.: WO2016/008257
PCT Pub. Date: Jan. 21, 2016

(30) Foreign Application Priority Data

Jul. 16, 2014 (CN) .......................... 2014 1 0339377

(51) Int. Cl.
*C07C 17/23* (2006.01)
*C07C 21/18* (2006.01)
*B01J 31/12* (2006.01)

(52) U.S. Cl.
CPC ............. *C07C 21/18* (2013.01); *B01J 31/121* (2013.01); *C07C 17/23* (2013.01)

(58) Field of Classification Search
CPC .................................................. C07C 17/25
See application file for complete search history.

(56) References Cited

U.S. PATENT DOCUMENTS

| 2,685,606 A | 8/1954 | Clark |
| 2,704,777 A | 3/1955 | Clark |
| 3,333,011 A | 7/1967 | Anello et al. |
| 2005/0261528 A1 | 11/2005 | Cottrell et al. |
| 2010/0268001 A1 | 10/2010 | Nappa |

FOREIGN PATENT DOCUMENTS

| CN | 1980974 A | 6/2007 |
| CN | 102395547 A | 3/2012 |
| EP | 0 416 015 B1 | 9/1993 |

OTHER PUBLICATIONS

Mori, T. et al. "Hydrodechlorination of 1,1,2-trichloro-1,2,2-trifluoroethane (CFC-113) over supported ruthenium and other noble metal catalysts" Catalysis Today 88 (2004) pp. 111-120.*
Wagoner, E. et al. "Electrocatalytic Reduction of 1,1,2-Trichloro-1,2,2-trifluoroethane (CFC-113) at Silver Cathodes in Organic and Organic-Aqueous Solvents" Journal of The Electrochemical Society, 160 (10) G135-G141 (2013).*

* cited by examiner

*Primary Examiner* — Medhanit Bahta
(74) *Attorney, Agent, or Firm* — Hudak, Shunk & Farine Co. LPA

(57) ABSTRACT

A process for preparing trifluorochloroethylene including: in a multi-tubular reactor, hydrogenation reacting 1,1,2-trifluoro-1,2,2-trichloroethane directly with a catalyst potassium zinc trihydride to obtain trifluorochloroethylene, wherein the catalytic reaction is performed at a temperature of 250-350° C. and a pressure of 0.7-1.0 MPa for 10-20 seconds. The conventional process in which zinc powder is used for dechlorination or hydrogen is used for dechlorination through hydrogenation with the action of a noble metal catalyst is avoided in the process disclosed herein. The present process substantially reduces the production cost of trifluorochloroethylene, and substantially increases the product yield, which can be up to 99% or more.

3 Claims, No Drawings

GREEN PREPARATION METHOD FOR TRIFLUOROCHLOROETHYLENE

FIELD OF THE INVENTION

The present invention relates to a process for preparing a compound, in particular, to a process for preparing trifluorochloroethylene.

TECHNICAL BACKGROUND OF THE INVENTION

Trifluorochloroethylene (CTFE) is an important special monomer for fluorine-containing high performance materials in which polytrifluorochloroethylene has superior oxygen isolating and low temperature resistant properties and thus is widely used in packaging films for medicine, electronics encapsulation applications and delivery tubes for low temperature materials. Additionally, fluorine-containing coatings with trifluorochloroethylene as the main monomer have superior weather resistant and corrosion resistant properties, and are widely used in building industries. Currently, the global annual output of trifluorochloroethylene is around 10,000 tons, and the primary process for preparing the same is to dechlorine from trifluorotrichloroethane with the action of zinc powder or hydrogen.

Since in the conventional process significant amount of zinc powder will be consumed when zinc powder is used for dechlorination, and meanwhile significant amount of zinc chloride waste residues will be generated, the production cost of trifluorochloroethylene would be increased a lot due to consumption of zinc powder and the need of treatment of the residues. When hydrogen is directly used for dechlorination, an expensive rare metal such as platinum, rhodium or ruthenium would be required as a catalyst, and therefore, the production cost is also relatively high. Meanwhile, hydrogenation by using hydrogen directly tends to result in excessive hydrogenation, and impurities such as trifluoroethylene may be generated, which would result in decrease of yield and purity of the product. The disadvantages of the processes disclosed in patent documents U.S. Pat. No. 2,685,606, U.S. Pat. No. 2,704,777, EP 0416015 and U.S. Pat. No. 3,333,011 have been summarized as above. Generally, the product cost of trifluorochloroethylene in these documents is relatively high, and the yield of product is relatively low, typically only about 85%.

SUMMARY OF THE INVENTION

The technical problem solved by the present invention is to provide a process for preparing trifluorochloroethylene, which is green, of low cost but high yield. In order to solve the above technical problem, the technical solution provided in the present invention is as follows:

A new green process for preparing trifluorochloroethylene comprising: in a multi-tubular reactor, hydrogenation reacting 1,1,2-trifluoro-1,2,2-trichloroethane directly with a catalyst potassium zinc trihydride to obtain trifluorochloroethylene, with the following chemical equation:

$$3CF_2ClCCl_2F + KZnH_3 \rightarrow 3ClFC=CF_2 + KZnCl_3 + 3HCl,$$

wherein the catalytic reaction is performed at a temperature of 250-350° C. and a pressure of 0.7-1.0 MPa for 10-20 seconds.

The catalyst can be reused upon activation by addition of hydrogen, and a process for activating the catalyst comprising: activating the catalyst with the action of hydrogen, with the following chemical equation:

$$KZnCl_3 + 3H_2 \rightarrow KZnH_3 + 3HCl,$$

wherein the activating is performed at a temperature of 200-300° C. and a pressure of 0.9-1.0 MPa for 5-10 seconds.

A process for preparing the catalyst potassium zinc trihydride comprising: dissolving potassium chloride in an deionized water to obtain a potassium chloride solution; dissolving zinc chloride in an deionized water to obtain a zinc chloride solution; adding dropwise the zinc chloride solution to the potassium chloride solution and reacting at 50-80° C. and atmosphere pressure for 5-10 hours to obtain a potassium zinc trihydride solution; evaporating the potassium zinc trihydride solution to obtain potassium zinc trihydride; treating the potassium zinc trihydride by hydrogenation directly using hydrogen, wherein the molar ratio of potassium zinc trihydride to hydrogen is 1:3 to 1:4, the temperature of the hydrogenation is 200-300° C., the reaction pressure is 0.9-1.0 MPa, and the reaction time is 5-10 seconds; the concentration of the potassium chloride solution is 20-32% by weight, the concentration of the zinc chloride is 50-82% by weight, and the conductivity of the deionized water is 0.01-0.02μ.

The conventional process in which zinc powder is used for dechlorination or hydrogen is used for dechlorination through hydrogenation with the action of a noble metal catalyst is avoided in the process of the present invention. The present process substantially reduces the production cost of trifluorochloroethylene, and substantially increases the product yield, which can be up to 99% or more.

DETAILED DESCRIPTION OF THE INVENTION

The products obtained in the Examples of the present invention were measured by a gas chromatography/mass-spectrography 6890N/5937 (GC/MS) from Agilent.

Potassium zinc trihydride is prepared using the following method: potassium chloride is dissolved in an deionized water (the conductivity of the deionized water is 0.01-0.02μ) to obtain a potassium chloride solution (the concentration of the potassium chloride solution is 20-32% by weight); zinc chloride is dissolved in an deionized water (the conductivity of the deionized water is 0.01-0.02μ) to obtain a zinc chloride solution (the concentration of the zinc chloride is 50-82% by weight); add dropwise the zinc chloride solution to the potassium chloride solution and have them react at 50-80° C. and atmosphere pressure for 5-10 hours to obtain a potassium zinc trihydride solution; the potassium zinc trihydride solution is subjected to evaporation to obtain potassium zinc trihydride; the potassium zinc trihydride is then subjected to a hydrogenation treatment, wherein the molar ratio of potassium zinc trihydride to hydrogen us 1:3 to 1:4, the temperature of the hydrogenation is 200-300° C., the reaction pressure is 0.9-1.0 MPa, and the reaction time is 5-10 seconds.

Example 1

21.4 Kg potassium zinc trihydride was placed in a multi-tubular reactor comprising six nickel alloy tubes each having a diameter of 40 mm and a length of 6,000 mm, and the catalyst was added in a volume of 30 L. The multi-tubular reactor jacket was heated with a thermal oil. The reactor was heated up to 250° C., and nitrogen was introduced at a rate of 10 L/min to further dry the catalyst. The introduction of nitrogen was continued for 5 hours, and then the reactor was further heated up to 300° C. 1,1,2-trifluo-1,2,2-trichloroethane was preheated and then fed into the multi-tubular reactor from the top thereof, with the feeding rate under standard state being 180 L/min. The pressure of the multi-tubular reactor was maintained at 0.8 MPa. The reacted materials were then discharged from the bottom of the multi-tubular reactor, washed directly with water and alkali, dried with a molecular sieve, condensed, collected by rectification, and then samples were taken and analyzed. After an hour, 56 Kg trifluorochloroethylene having a purity of 99.5% was obtained. The conversion ratio of 1,1,2-trifluo-1,2,2-trichloroethane was 99.0%, and the yield was 99.20%.

When the conversion ratio of 1,1,2-trifluo-1,2,2-trichloroethane and the yield began to decrease, stop feeding and began to feed hydrogen, with the temperature of the multi-tubular reactor being maintained at 300° C., the feeding rate of hydrogen under standard state being 360 L/min, and the pressure of the multi-tubular reactor being maintained at 0.9 MPa. After 30 minutes, the activation was completed, and the feeding was switched back. The feeding rate of 1,1,2-trifluo-1,2,2-trichloroethane was 180 L/min under standard state, and the pressure of the multi-tubular reactor was maintained at 0.8 MPa. The reacted materials were then discharged from the bottom of the multi-tubular reactor, washed directly with water and alkali, dried with a molecular sieve, condensed, collected by rectification, and then samples were taken and analyzed. After an hour, 55.9 Kg trifluorochloroethylene having a purity of 99.5% was obtained. The conversion ratio of 1,1,2-trifluo-1,2,2-trichloroethane was 99.1%, and the yield was 99.02%.

Example 2

21.4 Kg potassium zinc trihydride was placed in a multi-tubular reactor comprising six nickel alloy tubes having a diameter of 40 mm and a length of 6,000 mm, and the catalyst was added in a volume of 30 L. The multi-tubular reactor jacket was heated with a thermal oil. The reactor was heated up to 250° C., and nitrogen was introduced at a rate of 10 L/min to further dry the catalyst. The introduction of nitrogen was continued for 5 hours, and then the reactor was further heated up to 280° C. 1,1,2-trifluo-1,2,2-trichloroethane was preheated and then fed into the multi-tubular reactor from the top thereof, with the feeding rate under standard state being 120 L/min. The pressure of the multi-tubular reactor was maintained at 0.9 MPa. The reacted materials were then discharged from the bottom of the multi-tubular reactor, washed directly with water and alkali, dried with a molecular sieve, condensed, collected by rectification, and then samples were taken and analyzed. After an hour, 37.25 Kg trifluorochloroethylene having a purity of 99.60% was obtained. The conversion ratio of 1,1,2-trifluo-1,2,2-trichloroethane was 99.2%, and the yield was 99.07%.

When the conversion ratio of 1,1,2-trifluo-1,2,2-trichloroethane and the yield began to decrease, stop feeding and began to feed hydrogen, with the temperature of the multi-tubular reactor being maintained at 280° C., the feeding rate of hydrogen under standard state being 240 L/min, and the pressure of the multi-tubular reactor being maintained at 1.0 MPa. After 30 minutes, the activation was completed, and the feeding was switched back. The feeding rate of 1,1,2-trifluo-1,2,2-trichloroethane was 120 L/min under standard state, and the pressure of the multi-tubular reactor was maintained at 0.9 MPa. The reacted materials were then discharged from the bottom of the multi-tubular reactor, washed directly with water and alkali, dried with a molecular sieve, condensed, collected by rectification, and then samples were taken and analyzed. After an hour, 37.22 Kg trifluorochloroethylene having a purity of 99.70% was obtained. The conversion ratio of 1,1,2-trifluo-1,2,2-trichloroethane was 99.2%, and the yield was 99.09%.

Example 3

21.4 Kg potassium zinc trihydride was placed in a multi-tubular reactor comprising six nickel alloy tubes having a diameter of 40 mm and a length of 6,000 mm, and the catalyst was added in a volume of 30 L. The multi-tubular reactor jacket was heated with a thermal oil. The reactor was heated up to 250° C., and nitrogen was introduced at a rate of 10 L/min to further dry the catalyst. The introduction of nitrogen was continued for 5 hours, and then the reactor was further heated up to 320° C. 1,1,2-trifluo-1,2,2-trichloroethane was preheated and then fed into the multi-tubular reactor from the top thereof, with the feeding rate under standard state being 90 L/min. The pressure of the multi-tubular reactor was maintained at 1.0 MPa. The reacted materials were then discharged from the bottom of the multi-tubular reactor, washed directly with water and alkali, dried with a molecular sieve, condensed, collected by rectification, and then samples were taken and analyzed. After an hour, 27.90 Kg trifluorochloroethylene having a purity of 99.9% was obtained. The conversion ratio of 1,1,2-trifluo-1,2,2-trichloroethane was 99.5%, and the yield was 99.22%.

When the conversion ratio of 1,1,2-trifluo-1,2,2-trichloroethane and the yield began to decrease, stop feeding and began to feed hydrogen, with the temperature of the multi-tubular reactor being decreased to 300° C., the feeding rate of hydrogen under standard state being 180 L/min, and the pressure of the multi-tubular reactor being maintained at 0.9 MPa. After 30 minutes, the activation was completed, and the feeding was switched back. The feeding rate of 1,1,2-trifluo-1,2,2-trichloroethane was 90 L/min under standard state, and the pressure of the multi-tubular reactor was maintained at 1.0 MPa. The reacted material was then discharged from the bottom of the multi-tubular reactor, washed directly with water and alkali, dried with a molecular sieve, condensed, collected by rectification, and then samples were taken and analyzed. After an hour, 27.85 Kg trifluorochloroethylene having a purity of 99.91% was obtained. The conversion ratio of 1,1,2-trifluo-1,2,2-trichloroethane was 99.1%, and the yield was 99.06%.

The Examples as set forth above should not be construed as limiting the present invention in any way. It should be understood that any technical solutions obtained by equivalent substitutions or variations would fall within the scope of the present invention.

What is claimed is:

1. A process for preparing trifluorochloroethylene comprising reacting 1,1,2-trifluoro-1,2,2-trichloroethane directly with a catalyst potassium zinc trihydride in a multi-tubular reactor to obtain trifluorochloroethylene, wherein the catalytic reaction is performed at a temperature of 250-350° C. and a pressure of 0.7-1.0 MPa for 10-20 seconds.

2. The process for preparing trifluorochloroethylene according to claim 1, wherein the catalyst is reused upon activation by the addition of hydrogen.

3. The process for preparing trifluorochloroethylene according to claim 2, wherein the activation comprising activating the catalyst at a temperature of 200-300° C. and a pressure of 0.9-1.0 MPa for 5-10 seconds.

* * * * *